US010406312B2

(12) United States Patent
Flynn

(10) Patent No.: US 10,406,312 B2
(45) Date of Patent: Sep. 10, 2019

(54) CPAP FLOW DRIVER FOR USING NEBULIZER WITH CPAP APPARATUS

(71) Applicant: Stephen Donald Flynn, Oakville (CA)

(72) Inventor: Stephen Donald Flynn, Oakville (CA)

( * ) Notice: Subject to any disclaimer, the term of this patent is extended or adjusted under 35 U.S.C. 154(b) by 1360 days.

(21) Appl. No.: 14/520,336

(22) Filed: Oct. 21, 2014

(65) Prior Publication Data

US 2016/0106947 A1    Apr. 21, 2016

(51) Int. Cl.
| | | |
|---|---|---|
| *A61M 16/14* | (2006.01) | |
| *A61M 11/02* | (2006.01) | |
| *A61M 16/06* | (2006.01) | |
| *A61M 16/08* | (2006.01) | |
| *A61M 16/12* | (2006.01) | |
| *A61M 15/00* | (2006.01) | |
| *A61M 16/20* | (2006.01) | |
| *A61M 16/10* | (2006.01) | |

(52) U.S. Cl.
CPC ............ *A61M 16/14* (2013.01); *A61M 11/02* (2013.01); *A61M 16/06* (2013.01); *A61M 16/0816* (2013.01); *A61M 16/127* (2014.02); *A61M 15/009* (2013.01); *A61M 16/107* (2014.02); *A61M 16/208* (2013.01)

(58) Field of Classification Search
CPC .. A61M 16/14; A61M 16/127; A61M 16/125; A61M 11/02; A61M 11/04; A61M 16/06; A61M 16/0816; A61M 16/105; A61M 16/107; A61M 15/009; A61M 16/208; A61M 15/0065; B65D 83/52; B65D 83/525; B65D 83/54; B65D 83/543; B65D 83/546

USPC .................................................... 128/203.12
See application file for complete search history.

(56) References Cited

U.S. PATENT DOCUMENTS

| | | | |
|---|---|---|---|
| 4,592,349 A * | 6/1986 | Bird ...................... | A61M 16/08 128/204.25 |
| 5,237,987 A | 8/1993 | Anderson et al. | |
| 7,721,735 B2 | 5/2010 | Hamilton et al. | |
| 2003/0217749 A1 | 11/2003 | Dougill | |

FOREIGN PATENT DOCUMENTS

| | | |
|---|---|---|
| FR | 2915106 B3 | 3/2009 |
| JP | 3860327 B2 | 12/2006 |

OTHER PUBLICATIONS

J. Yasushi, Translation of Japanese Publication JP11-267216 related to JP3860327, Published Oct. 5, 1999, 35 pages.
Machine Translation of FR2915106, 10 pages.

* cited by examiner

*Primary Examiner* — Jan Christopher L Merene
*Assistant Examiner* — Elliot S Ruddie
(74) *Attorney, Agent, or Firm* — Benesch, Friedlander, Coplan & Aronoff, LLP

(57) ABSTRACT

A CPAP flow driver is adapted to split supplied breathable fluid into a first portion delivered to a venturi throat to generate a pressure drop to draw in ambient air to create a CPAP flow and a second portion that is delivered to a nebulizer to drive the nebulizer.

9 Claims, 7 Drawing Sheets

CPAP FLOW DRIVER FOR USING NEBULIZER WITH CPAP APPARATUS

TECHNICAL FIELD

Figure 1:
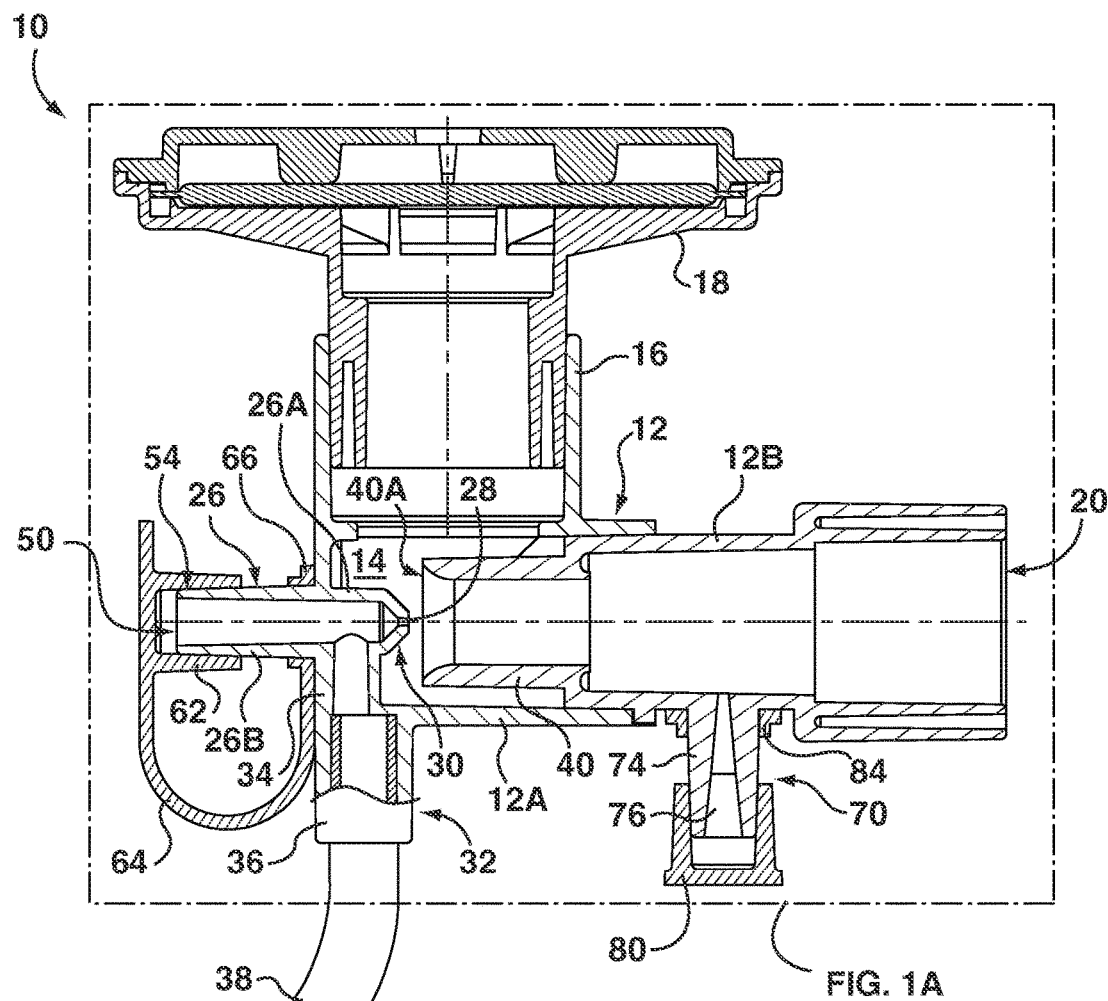
Figure 1:
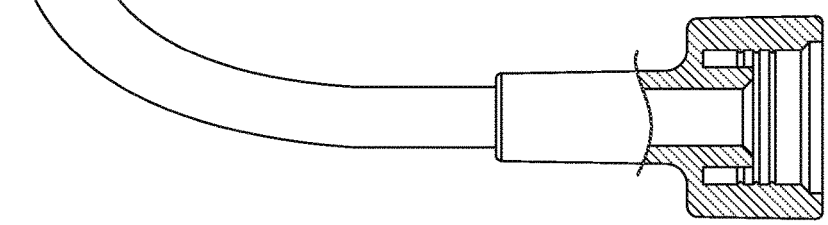

The present disclosure relates to continuous positive airway pressure (CPAP) apparatus, and more particularly to the integration of CPAP apparatus with a nebulizer for administering medication.

BACKGROUND

CPAP devices, originally used for treating sleep apnea, are now also used to treat respiratory distress. In this latter application, medication may be fed into the airflow using a nebulizer. A nebulizer is a device having a reservoir of liquid medicament and which uses a source of pressurized gas, such as oxygen or compressed air, to disperse the medicament into aerosol droplets which can be inhaled by a patient. Thus, when used in combination with a CPAP apparatus, the aerosol droplets generated by the nebulizer can be combined with the breathable fluid delivered to the patient via the CPAP apparatus. The CPAP apparatus and the nebulizer each require a source of pressurized breathable fluid in order to operate. Thus, conventionally, two distinct sources of pressurized breathable fluid have been required when a nebulizer is to be used in conjunction with a CPAP apparatus. U.S. Patent Application Publication No. 2003/0217749 discloses an apparatus for delivering a breathable gas together with a nebulised medicament to a patient using a single gas cylinder, but requires that two separate lines be connected to the gas cylinder.

SUMMARY

The present disclosure describes an arrangement in which a portion of the breathable fluid supplied to a CPAP flow driver is diverted to drive a nebulizer.

In one aspect, the present disclosure relates to a flow driver for CPAP applications. The flow driver comprises an outer housing enclosing an interior volume, an ambient air inlet in fluid communication with the interior volume, and a CPAP mask fluid supply outlet in fluid communication with the interior volume and adapted to be coupled to a CPAP mask. A guide tube extends into the interior volume and has a constriction aperture at one end thereof, with the constriction aperture disposed inside the housing. A fluid supply inlet is in fluid communication with the guide tube and is otherwise isolated from the interior volume, and a venturi throat is disposed inside the housing. The venturi throat is larger than the constriction aperture and is arranged in fluid communication with the constriction aperture, the ambient air inlet and the CPAP mask fluid supply outlet via the interior volume. The constriction aperture and the ambient air inlet are disposed upstream of the venturi throat and the CPAP mask fluid supply outlet is disposed downstream of the venturi throat. The constriction aperture and the venturi throat cooperate to generate, for fluid flow from the constriction aperture into the venturi throat, a pressure drop across the venturi throat to draw fluid from the ambient air intake into the venturi throat. The flow driver is characterized in that a nebulizer supply outlet is disposed at the end of the guide tube opposite the constriction aperture, with the nebulizer supply outlet adapted to be coupled in fluid communication to a nebulizer inlet for driving a nebulizer, and the guide tube is adapted to split fluid received from the fluid supply inlet into a nebulizer supply portion and a CPAP supply portion and to guide the nebulizer supply portion toward the nebulizer supply outlet and to guide the CPAP supply portion through the constriction aperture toward the venturi throat.

The ambient air inlet may be adapted to removably receive a filter assembly.

The flow driver may further comprise an MDI port communicating with the interior volume of the housing downstream of the venturi throat and upstream of the CPAP mask fluid supply outlet.

In certain embodiments, the interior volume of the housing may be in fluid communication with an airway pressure gauge downstream of the venturi throat and upstream of the CPAP mask fluid supply outlet. The airway pressure gauge may be carried by the housing.

In another aspect, the present disclosure relates to a method for operating a CPAP mask in conjunction with a nebulizer. The method comprises supplying breathable fluid to a guide tube, feeding a first portion of the breathable fluid from one end of the guide tube into a venturi throat coupled in fluid communication with the CPAP mask to draw ambient air through an ambient air inlet into the venturi throat and supply CPAP fluid to the CPAP mask via a venturi effect, and feeding a second portion of the breathable fluid from the other end of the guide tube to a nebulizer coupled in fluid communication with the CPAP mask to drive the nebulizer.

BRIEF DESCRIPTION OF THE DRAWINGS

These and other features of the disclosure will become more apparent from the following description in which reference is made to the appended drawings wherein:

FIG. 1 is a side cross-sectional view of a first exemplary flow driver showing the flow driver coupled to a fluid supply hose;

FIG. 1A is a detailed side cross-sectional view of the flow driver of FIG. 1;

FIG. 2 is a top plan cross-sectional view of the low driver of FIG. 1;

FIG. 3 is a side view of the flow driver of FIG. 1 coupled to a CPAP mask via a nebulizer adaptor and also coupled to a nebulizer;

FIG. 3A is a side view of the arrangement shown in FIG. 3 also showing use of a metered dose inhaler with the flow driver of FIG. 1;

FIG. 4 is a side view of the arrangement shown in FIG. 3 showing the flow driver of FIG. 1 in cross-section; and FIG. 5 is a side view of a second exemplary flow driver coupled to a CPAP mask via a CPAP adaptor and nebulizer adaptor and also coupled to a nebulizer.

DETAILED DESCRIPTION

Reference is now made to FIGS. 1 and 1A, in which an exemplary flow driver 10 for use in CPAP applications is shown in cross-section. The flow driver 10 is in many respects similar to conventional CPAP flow drivers, and uses a venturi effect to combine incoming pressurized breathable fluid (typically air or oxygen-enriched air) with ambient air to generate a desired flow for delivery to a CPAP mask.

The flow driver 10 comprises a generally tubular outer housing 12 enclosing an interior volume 14. In the illustrated embodiment, the outer housing 12 comprises a generally tubular inlet portion 12A and a generally tubular outlet portion 12B sealingly secured together. An ambient air inlet in the form of a tube 16 is formed in the housing 12, in fluid communication with the interior volume 14. The tube 16 forming the ambient air inlet is adapted to removably receive a suitable filter assembly 18 as shown to filter any air leaving the interior volume 14 through the tube 16 (e.g. exhaled air). The filter assembly 18 may be conventional in structure and is not described further.

Figure 3:
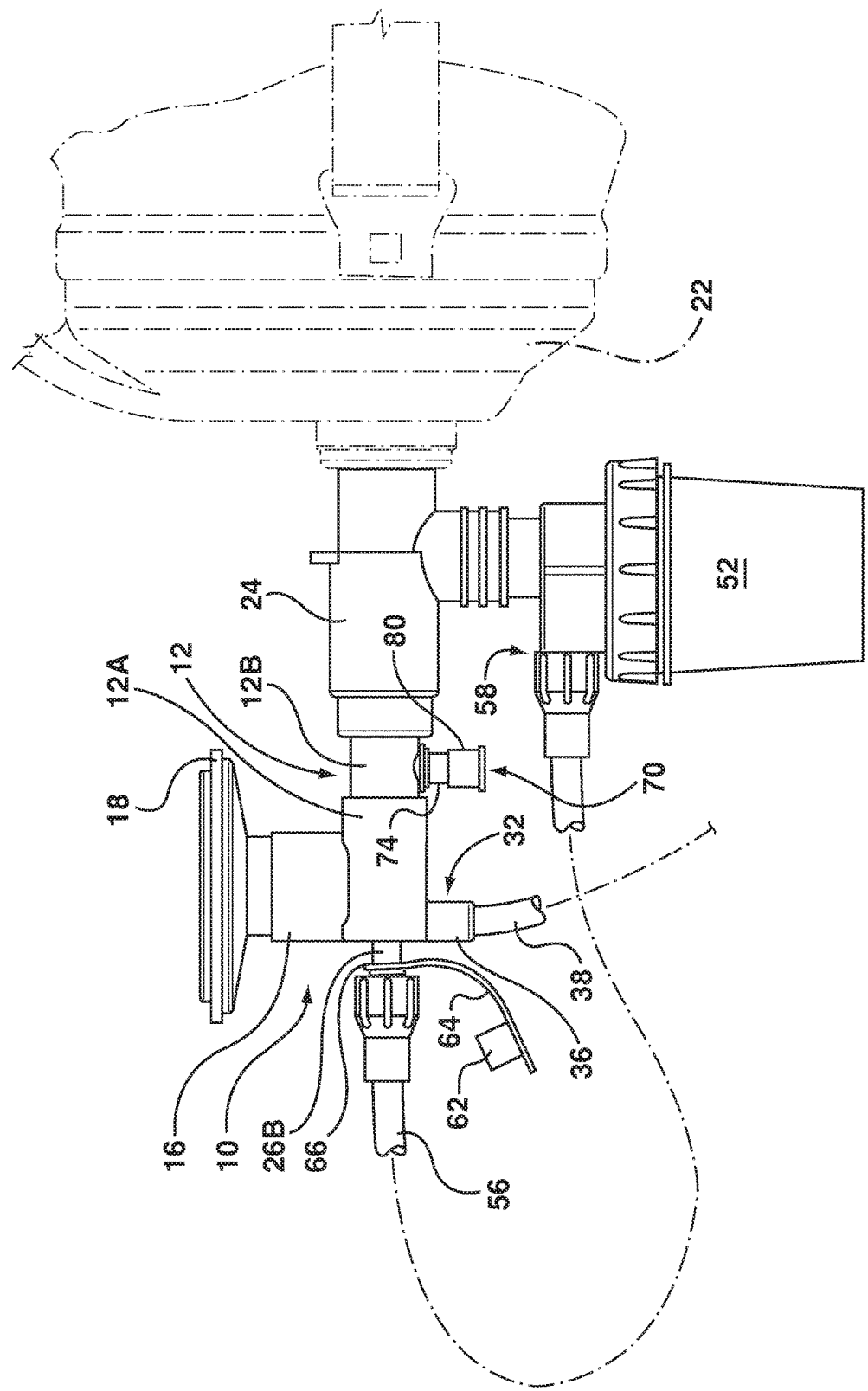
Figure 3A:
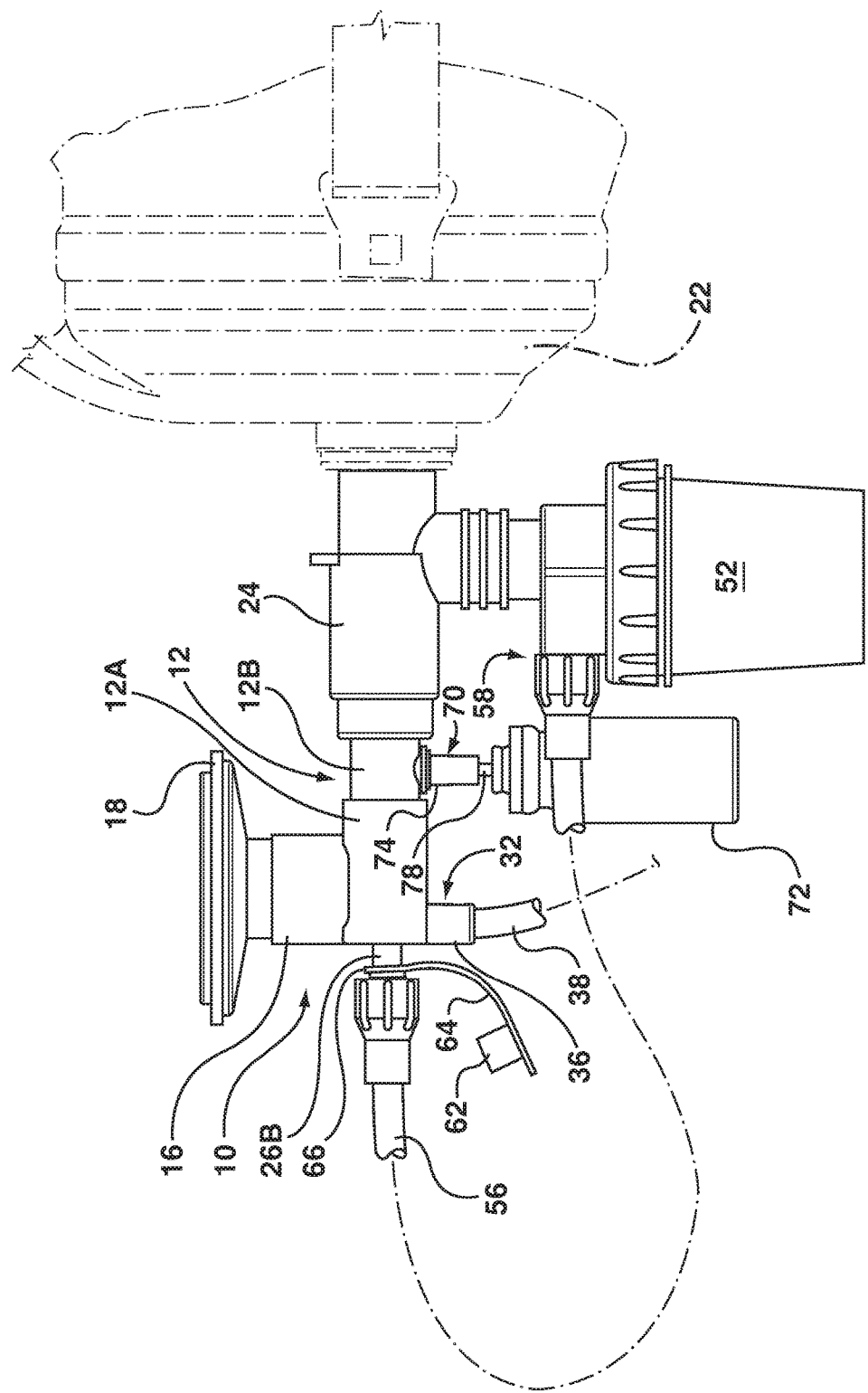
Figure 4:
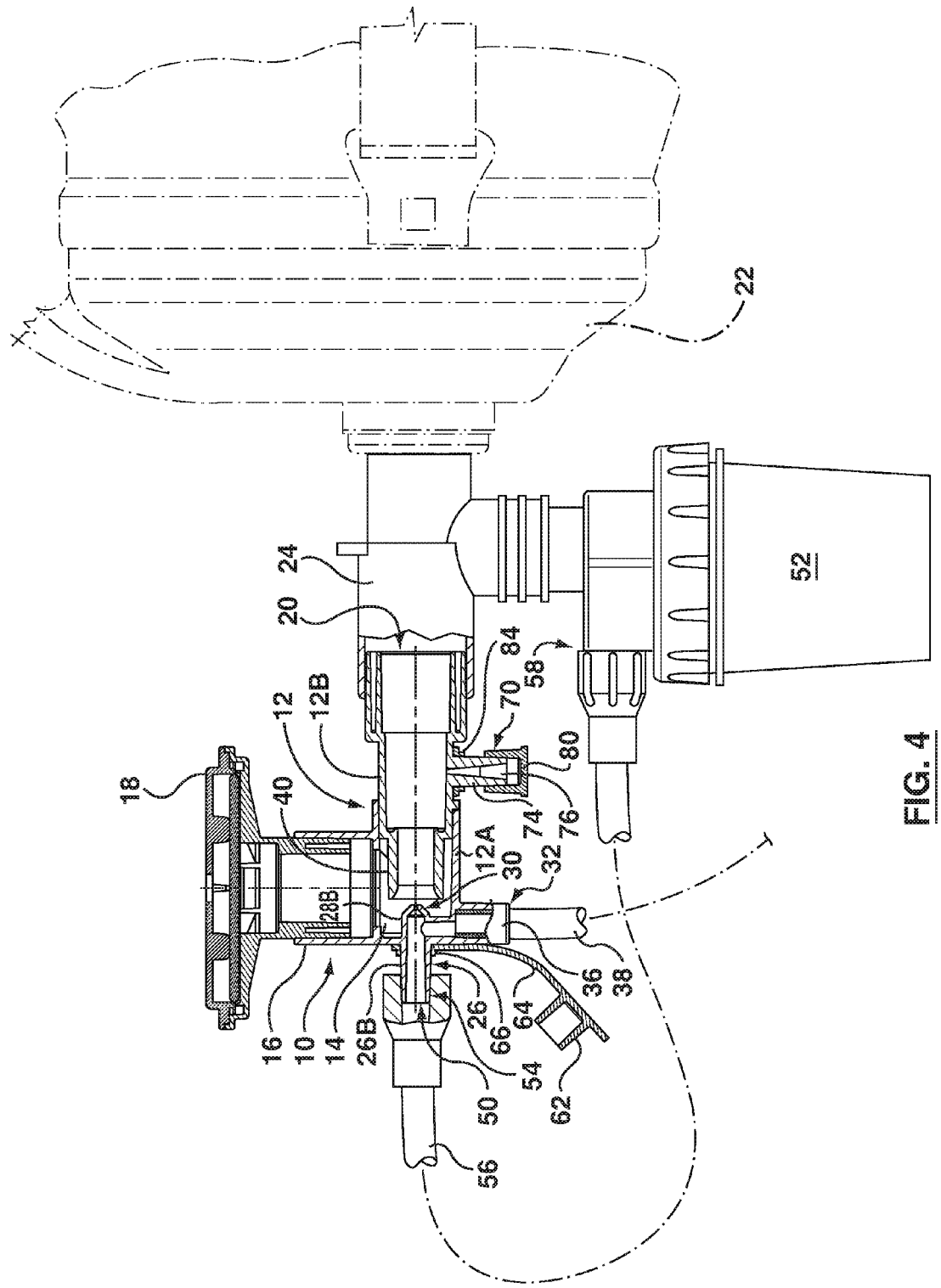

A CPAP mask fluid supply outlet 20 is formed at the end of the outlet portion 12B of the housing 12 that is remote from the end of the outlet portion 12B of the housing 12 that is secured to the inlet portion 12A of the housing 12. The CPAP mask fluid supply outlet 20 is in fluid communication with the interior volume 14 and is adapted to be coupled, either directly or indirectly, to a CPAP mask. For example, as shown in FIGS. 3, 3A and 4, the CPAP mask fluid supply outlet 20 is coupled to a CPAP mask 22 by way of an intervening nebulizer adaptor 24. The CPAP mask 22 and nebulizer adaptor 24 are of conventional design and are not described further.

A guide tube 26 is formed in the inlet portion 12A of the housing 12, at the end thereof opposite the end that is secured to the outlet portion 12B of the housing 12. An inlet portion 26A of the guide tube 26 extends into the interior volume 14. The guide tube 26 has a constriction aperture 28 at the terminal end 30 of the inlet portion 26A; this end 30, and hence the constriction aperture 28, is disposed inside the housing 12 and hence inside the interior volume 14. A fluid supply inlet 32 is formed in the inlet portion 12A of the housing 12; the fluid supply inlet 32 is in fluid communication with the guide tube 26 and is otherwise isolated from the interior volume 14. In the illustrated embodiment, the fluid supply inlet 32 comprises an interior tube 34 disposed inside the inlet portion 12A of the housing 12 in fluid communication with the inlet portion 26A of the guide tube 26 and a connector tube 36 extending outwardly from the inlet portion 12A of the housing 12, exteriorly thereof. The connector tube 36 sealingly receives a fluid supply hose 38, and is in fluid communication with the connector tube 36 to deliver fluid from the fluid supply hose 38 to the inlet portion 26A of the guide tube 26 via the connector tube 36 and the interior tube 34. The fluid supply hose 38 will be in fluid communication with a source of pressurized breathable fluid, typically air or oxygen-enriched air, such as a pump or gas cylinder.

A venturi throat 40 is disposed inside the housing 12. As can be seen, the venturi throat 40 is substantially larger in diameter than the constriction aperture 28. In the illustrated embodiment, the venturi throat 40 is formed as part of the outlet portion 12B of the housing 12 and comprises a tube extending into the inlet portion 12A of the housing 12. The venturi throat 40 is arranged in fluid communication with the constriction aperture 28, the tube 16 forming the ambient air inlet, and the CPAP mask fluid supply outlet 20, via the interior volume 14. The constriction aperture 28 and the tube 16 forming the ambient air inlet are disposed upstream of the venturi throat 40 and the CPAP mask fluid supply outlet 20 is disposed downstream of the venturi throat 40. Thus, the venturi throat 40 is positioned between the guide tube 26 and the CPAP mask fluid supply outlet 20. As can be seen, the terminal end 30 of the guide tube 26, and hence the constriction aperture 28, is spaced from the opening 40A of the venturi throat 40. When fluid flows from the constriction aperture 28 into the venturi throat 40, the constriction aperture 28 and the venturi throat 40 cooperate to generate a pressure drop across the venturi throat 40. This pressure drop draws ambient fluid $F_{AMBIENT}$ (i.e. air) through the tube 16 forming the ambient air intake from outside of the housing 12 into the interior volume 14 and then into the venturi throat 40.

The flow driver 10 differs from conventional CPAP flow drivers in that it includes a nebulizer supply outlet 50 and can divert a portion of the breathable fluid supplied to the fluid supply inlet 32 via the fluid supply hose 38 through the nebulizer supply outlet 50 to drive a nebulizer 52 (FIGS. 3 to 4).

In the illustrated embodiment, a connection portion 26B of the guide tube 26 extends outwardly from the inlet portion 12A of the housing 12A, exteriorly thereof, and the nebulizer supply outlet 50 is formed by the open terminal end 54 of the connection portion 26B of the guide tube 26. Thus, the nebulizer supply outlet 50 is disposed at the end 54 of the guide tube 26 opposite the constriction aperture 28. As can be seen in FIG. 1A, the guide tube 26 is adapted to split breathable fluid F received from the fluid supply inlet 32 into a nebulizer supply portion $F_{NEBULIZER}$ and a CPAP supply portion $F_{CPAP}$ and to guide the nebulizer supply portion $F_{NEBULIZER}$ toward the nebulizer supply outlet 50 and to guide the CPAP supply portion $F_{CPAP}$ through the constriction aperture 28 toward the venturi throat 40.

Referring now to FIGS. 3 to 4, the nebulizer supply outlet 50 is adapted to be coupled in fluid communication to a nebulizer inlet for driving a nebulizer. In the illustrated embodiment, the connection portion 26B of the guide tube 26 is sized to permit a conventional nebulizer connection hose 56 to be sealingly friction fit thereon to supply breathable fluid to a to a nebulizer inlet 58. As shown in FIGS. 3 to 4, the exemplary flow driver 10 may be coupled to a CPAP mask 22 by way of an intervening nebulizer adaptor 24. A conventional nebulizer 52 may be coupled to the nebulizer adaptor 24 in known manner, and a conventional nebulizer connection hose 56 may be connected in fluid communication between the nebulizer supply outlet 50 and the nebulizer inlet 58, as shown. When pressurized breathable fluid F is supplied to the flow driver 10 from the fluid supply hose 38 via the fluid supply inlet 32, the breathable fluid F flows into the guide tube 26, which splits the breathable fluid F into a nebulizer supply portion $F_{NEBULIZER}$ and a CPAP supply portion $F_{CPAP}$. When the nebulizer inlet 58 is coupled (via the nebulizer connection hose 56) to nebulizer supply outlet 50 (see FIGS. 3 to 4), the nebulizer supply portion $F_{NEBULIZER}$ flows through the connection portion 26B of the guide tube 26 to and through the nebulizer supply outlet 50, into and through the nebulizer connection hose 56, and into the nebulizer inlet 58 to drive the nebulizer. The CPAP supply portion $F_{CPAP}$ flows through the inlet portion 26A of the guide tube 26 and then through the constriction aperture 28 toward the venturi throat 40 to generate, via venturi effect, a primary CPAP fluid flow, consisting of a mixture of the CPAP supply portion $F_{CPAP}$ and the ambient fluid $F_{AMBIENT}$. The primary CPAP fluid flow travels through the CPAP mask fluid supply outlet 20 and into the nebulizer adaptor 24, where the nebulizer supply portion $F_{NEBULIZER}$, now carrying entrained medication from the nebulizer 52, is admixed into the primary CPAP fluid flow for delivery to the CPAP mask 22.

Thus, the exemplary flow driver 10 enables and implements a method for operating CPAP mask 22 in conjunction with a nebulizer 52. The method comprises supplying breathable fluid F to a guide tube 26. The method further comprises feeding a first portion $F_{CPAP}$ of the breathable fluid F from one end 30 of the guide tube 26 into a venturi throat 40 coupled in fluid communication with the CPAP mask to draw ambient air through the ambient air inlet formed by the tube 16 into the venturi throat 40 and supply CPAP fluid $F_{CPAP}$ to the CPAP mask 22 via a venturi effect. The method still further comprises feeding a second portion $F_{NEBULIZER}$ of the breathable fluid F from the other end 54 of the guide tube 26 to drive the nebulizer 52, which is coupled in fluid communication with the CPAP mask 22.

Figure 1A:
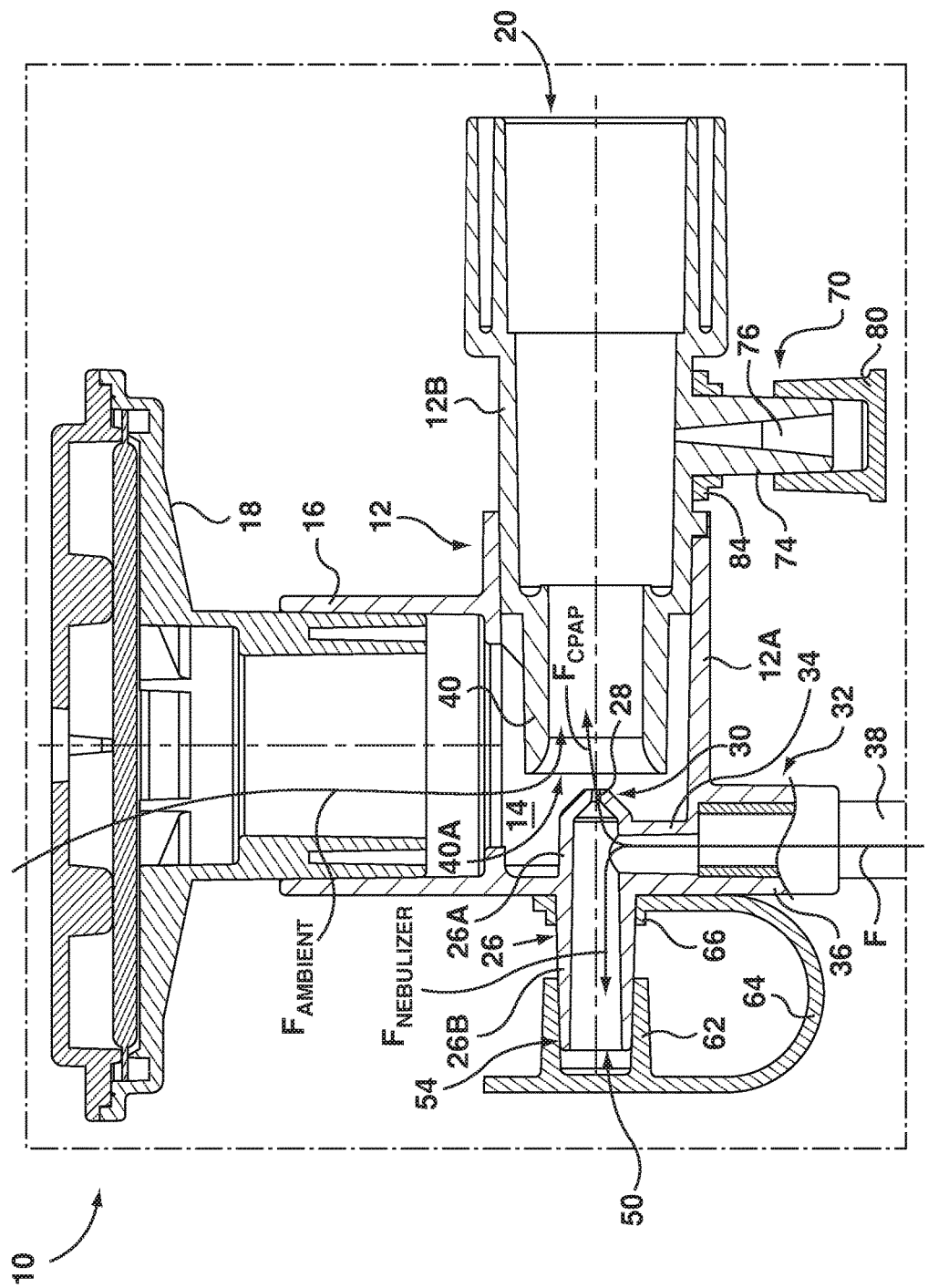
Figure 2:
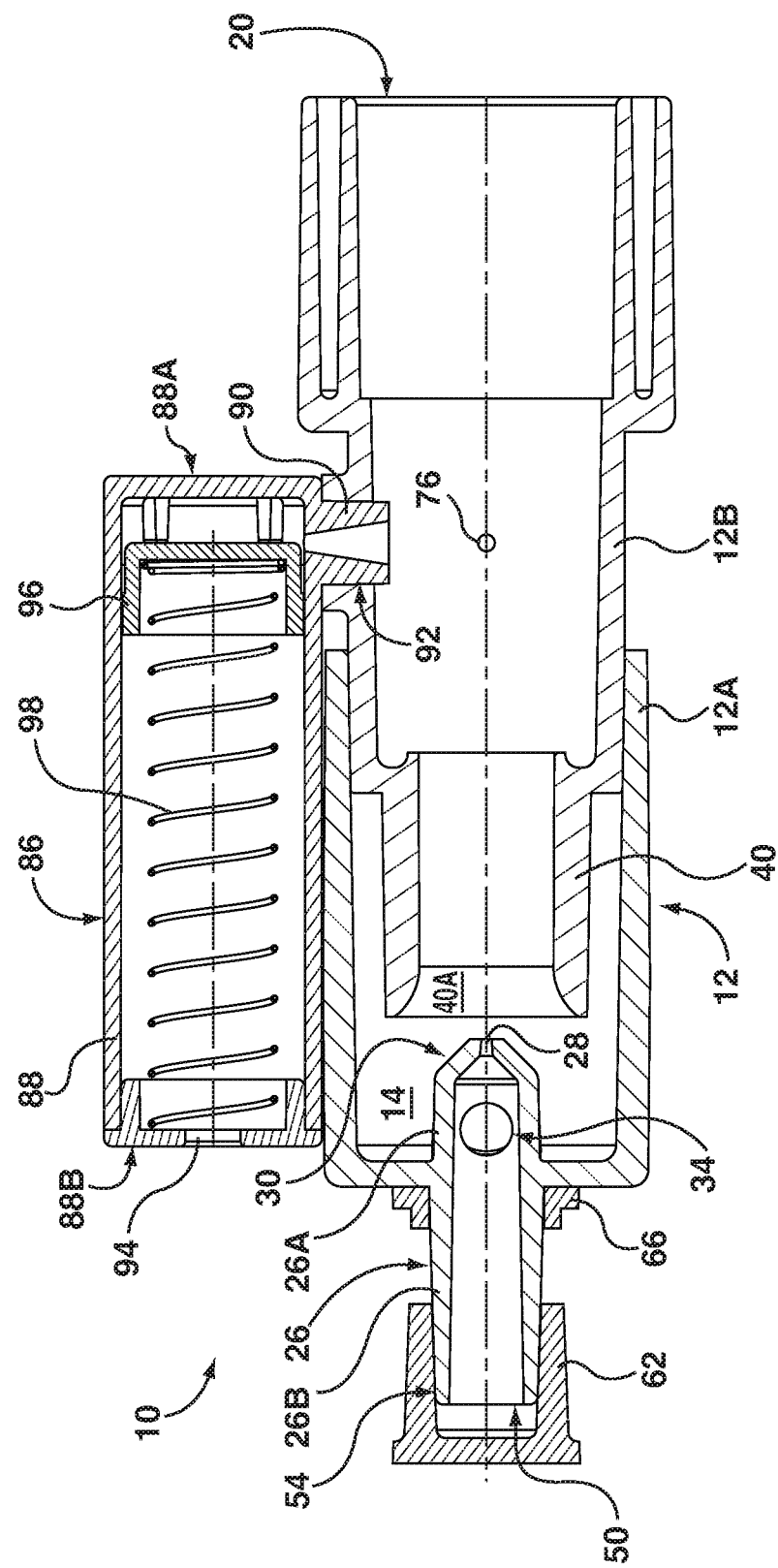

When the nebulizer 52 is not in use, the nebulizer connection hose 56 may be removed from the connection portion 26B of the guide tube 26, and a removable nebulizer supply outlet cap 62 may be friction fit over the connection portion 26B of the guide tube 26 to seal the nebulizer supply outlet 50, as shown in FIGS. 1 to 2. With the nebulizer supply outlet 50 sealed, most of the incoming breathable fluid F from the fluid supply inlet 32 will flow into the inlet portion 26A of the guide tube 26 as the CPAP supply portion $F_{CPAP}$ and a small portion of the incoming breathable fluid F will enter the connection portion 26B of the guide tube 26 as the nebulizer supply portion $F_{NEBULIZER}$ but is inhibited from passing through the nebulizer supply outlet 50 by the nebulizer supply outlet cap 62. In a preferred embodiment, the nebulizer supply outlet cap 62 is connected by way of a flexible tether 64 to a retention ring 66 that is friction fit onto the connection portion 26B of the guide tube 26.

The exemplary flow driver 10 includes a metered dose inhaler (MDI) port 70 to enable medication from a metered dose inhaler 72 to be administered, as shown in FIG. 3A. The MDI port extends outwardly from the outlet portion 12B of the housing 12 and communicates with the interior volume 14 of the housing 12 downstream of the venturi throat 40 and upstream of the CPAP mask fluid supply outlet 20. The MDI port 70 comprises an MDI tube 74 whose lumen 76 tapers frustoconically inwardly toward the housing 12 to provide a bearing surface for the valve stem 78 of the metered dose inhaler 72 (FIG. 3A). Similarly to the nebulizer supply outlet 50, the MDI port 70 may be provided with a removable MDI port cap 80 that can be friction fit over the MDI tube 74; preferably the MDI port cap 80 is connected by way of a flexible tether (not shown) to a retention ring 84 that is friction fit onto the MDI tube 74.

Referring now to FIG. 2, in the illustrated embodiment the housing 12 carries an airway pressure gauge 86 for measuring the pressure supplied to the CPAP mask 22; adjustments can be made at the source of the breathable fluid supplied via the fluid supply hose 38. The airway pressure gauge 86 comprises a generally tubular body 88 secured to the housing 12. At a first end 88A of the tubular body 88, a pressure measurement tube 90 extends through and is sealed in a pressure measurement aperture 92 formed in the outlet portion 12B of the housing 12, and a relief aperture 94 is formed through the other (second) end 88B of the tubular body 88. Thus, the airway pressure gauge 86 is in fluid communication with the interior volume 14 of the housing 12, downstream of the venturi throat 40 and upstream of the CPAP mask fluid supply outlet 20. An indicator member 96 is slidably received in the tubular body 88 and biased toward the end 88A having the pressure measurement tube 90 by a spring 98 acting between the indicator member 96 and the other end 88B of the tubular body 88. When in use, a portion of the CPAP supply portion $F_{CPAP}$ will pass through pressure measurement tube 90 into the tubular body 88 and push the indicator member 96 toward the end of the tubular body 88 remote from the end having the pressure measurement tube 90; ambient air between the indicator member 96 and the end 88B having the relief aperture 94 escapes through the relief aperture 94. The tubular body 88 is provided with pressure indicator markings and is at least partially transparent so that at least part of the indicator member 96 is visible therethrough, with the position of the indicator member 96, or of a marking thereon, being indicative of the pressure of the CPAP supply portion $F_{CPAP}$.

Figure 5:
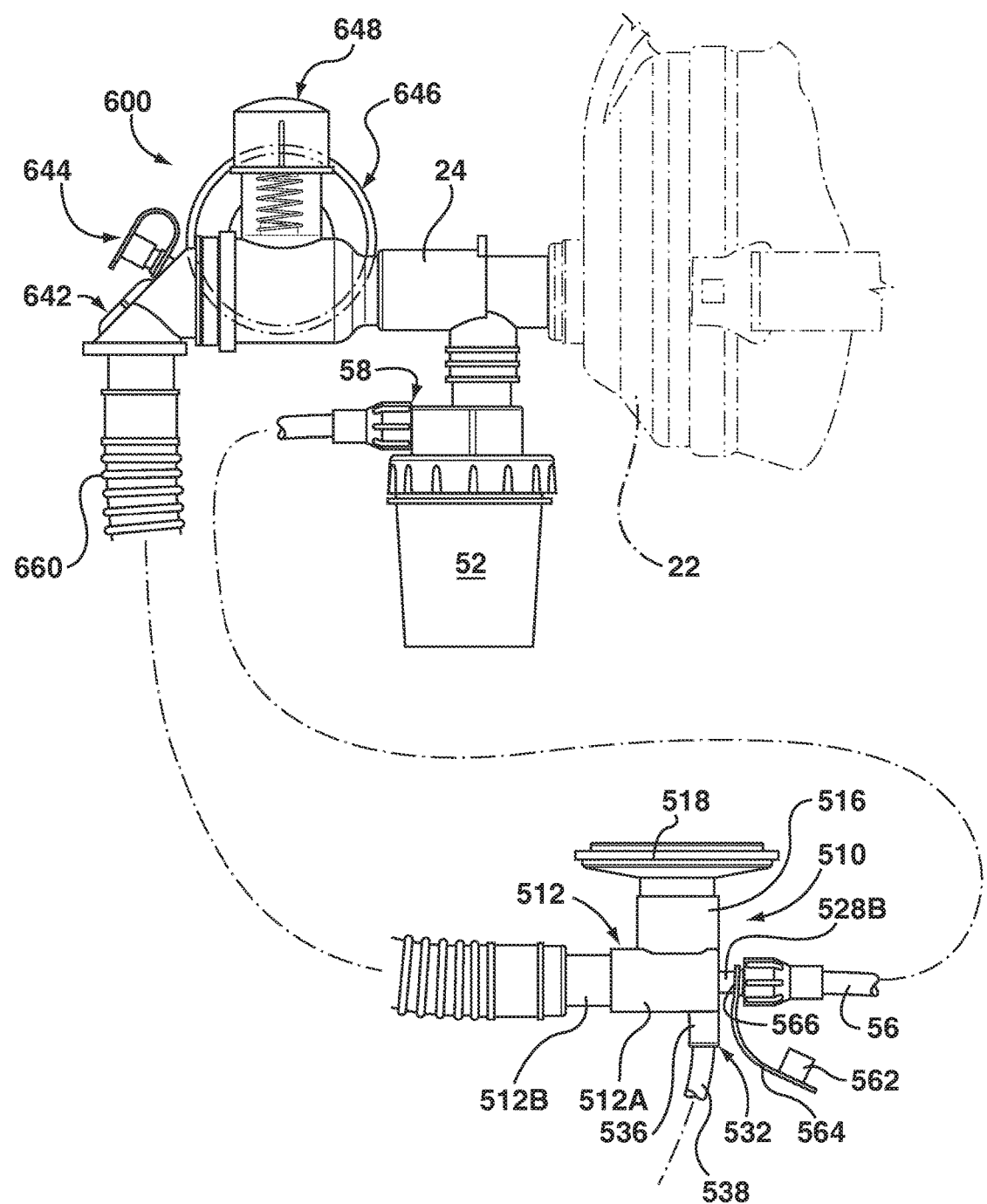

The first exemplary flow driver 10 described above includes an MDI port 70 and an airway pressure gauge 86, and may be used instead of a conventional CPAP adaptor, as shown in FIGS. 3 to 4. Flow drivers according to the present disclosure may also be used conjunction with a conventional CPAP adaptor 600, as shown in FIG. 5. The exemplary CPAP adaptor 600 may be, for example, one of the CPAP adaptors forming part of the Rescuer™ Emergency CPAP System of the type offered by BLS Systems Limited, having an address at 1124 South Service Rd W, Ontario, Canada L6L 5T7. The CPAP adaptor 600 shown in FIG. 5 includes an anti-asphyxia valve 642, an MDI port 644, a removable filter assembly 646 and a pressure adjustment mechanism 648 and, being conventional design, is not described further. The exemplary CPAP adaptor 600 is coupled to a CPAP mask 22 by way of an intervening nebulizer adaptor 24 to which is mounted a nebulizer 52. The CPAP mask 22, nebulizer adaptor 24, nebulizer 52 and nebulizer connection hose 56 shown in FIG. 5 are identical to the CPAP mask 22, nebulizer adaptor 24 and nebulizer 52 shown in FIGS. 3 to 4 and hence the same reference numerals are used.

A second exemplary flow driver 510 is coupled to the CPAP adaptor 600 via a flexible main hose 660. The second exemplary flow driver 510 shown in FIG. 5 is similar to the first exemplary flow driver 10 shown in FIGS. 1 to 4, with like reference numerals denoting like features except with the prefix "5". The second exemplary flow driver 510 shown in FIG. 5 differs from the first exemplary flow driver 10 shown in FIGS. 1 to 4 in that the second exemplary flow driver 510 does not include an MDI port or an airway pressure gauge since the CPAP adaptor 600 includes an MDI port 644, a removable filter 646 and a pressure adjustment mechanism 648. Thus, the MDI port and the airway pressure gauge forming part of the first exemplary flow driver 10 shown in FIGS. 1 to 4, while preferable, are optional and may be omitted from flow drivers constructed according to the present disclosure.

As shown in FIG. 5, the main hose 660 is coupled to the CPAP mask fluid supply outlet 520 of the flow driver 510, so that the CPAP mask fluid supply outlet 520 is coupled (indirectly via the main hose 660, CPAP adaptor 600 and nebulizer adaptor 24) to the CPAP mask 22. As with the first exemplary flow driver 10, a conventional nebulizer connection hose 56 may be connected in fluid communication between the nebulizer supply outlet 550 of second exemplary flow driver 510 and the nebulizer inlet 58 of the nebulizer 52 to drive the nebulizer 52.

It is to be understood that the CPAP adaptor, CPAP mask, nebulizer adaptor and nebulizer shown and described herein are merely exemplary and are presented for illustrative purposes only; flow drivers according to the present disclosure may be used in conjunction with other types of CPAP adaptors, CPAP masks, nebulizer adaptors and nebulizers and no limitation is intended or implied.

One or more currently preferred embodiments have been described by way of example. It will be apparent to persons skilled in the art that a number of variations and modifications can be made without departing from the scope of the claims.

What is claimed is:
1. An apparatus comprising:
  a flow driver for CPAP applications, wherein the flow driver comprises:
    an outer housing enclosing an interior volume;
    an ambient air inlet in fluid communication with the interior volume; and a CPAP mask fluid supply outlet in fluid communication with the interior volume and adapted to be coupled to a CPAP mask;
a guide tube extending into the interior volume and having a constriction aperture at one end thereof, the constriction aperture disposed inside the housing;
a fluid supply inlet in fluid communication with the guide tube and otherwise isolated from the interior volume;
a venturi throat disposed inside the housing, the venturi throat being larger than the constriction aperture and arranged in fluid communication with the constriction aperture, the ambient air inlet and the CPAP mask fluid supply outlet via the interior volume;
the constriction aperture and the ambient air inlet being disposed upstream of the venturi throat and the CPAP mask fluid supply outlet being disposed downstream of the venturi throat;
the constriction aperture and the venturi throat cooperating to generate, for fluid flow from the constriction aperture into the venturi throat, a pressure drop across the venturi throat to draw fluid from the ambient air intake into the venturi throat;

a nebulizer supply outlet is disposed at the end of the guide tube opposite the constriction aperture, the nebulizer supply outlet adapted to be coupled in fluid communication to a nebulizer inlet for driving a nebulizer;

wherein the guide tube is adapted to split fluid received from the fluid supply inlet into a nebulizer supply portion and a CPAP supply portion and to guide the nebulizer supply portion toward the nebulizer supply outlet and to guide the CPAP supply portion through the constriction aperture toward the venturi throat; and a metered dose inhaler (MDI) port communicating with the interior volume of the housing downstream of the venturi throat and upstream of the CPAP mask fluid supply outlet and adapted to receive an MDI dose for inhalation.

2. The apparatus of claim 1, wherein the ambient air inlet is adapted to removably receive a filter assembly.

3. The apparatus of claim 2, wherein the interior volume of the housing is in fluid communication with an airway pressure gauge downstream of the venturi throat and upstream of the CPAP mask fluid supply outlet.

4. The apparatus of claim 3, wherein the airway pressure gauge is carried by the housing.

5. The apparatus of claim 1, wherein the interior volume of the housing is in fluid communication with an airway pressure gauge downstream of the venturi throat and upstream of the CPAP mask fluid supply outlet.

6. The apparatus of claim 5, wherein the airway pressure gauge is carried by the housing.

7. The apparatus of claim 1, further comprising a metered dose inhaler having a valve stem received in the MDI port.

8. The apparatus of claim 7, wherein the MDI port comprises an MDI tube having a lumen that tapers frustoconically inwardly toward the housing to provide a bearing surface for the valve stem.

9. The apparatus of claim 1, wherein the MDI port comprises an MDI tube having a lumen that tapers frustoconically inwardly toward the housing to provide a bearing surface for a valve stem of a metered dose inhaler.

* * * * *